(12) United States Patent
Chan et al.

(10) Patent No.: US 9,889,113 B2
(45) Date of Patent: *Feb. 13, 2018

(54) METHOD FOR REVERSING, PREVENTING, DELAYING OR STABILIZING SOFT TISSUE CALCIFICATION

(71) Applicant: Panion & BF Biotech, Inc., Taipei (TW)

(72) Inventors: Keith Chan, Rockville, MD (US); Winston Town, Hong Kong (HK); Shou Shan Chiang, Taipei (TW)

(73) Assignee: Panion & BF Biotech Inc. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/694,876

(22) Filed: Sep. 4, 2017

(65) Prior Publication Data
US 2017/0368016 A1 Dec. 28, 2017

Related U.S. Application Data

(63) Continuation of application No. 12/162,558, filed as application No. PCT/US2007/002157 on Jan. 26, 2007, now Pat. No. 9,750,715.

(60) Provisional application No. 60/763,253, filed on Jan. 30, 2006.

(51) Int. Cl.
| | | |
|---|---|---|
| A61K 31/295 | (2006.01) | |
| A61K 9/14 | (2006.01) | |
| A61K 33/26 | (2006.01) | |
| A61K 31/555 | (2006.01) | |

(52) U.S. Cl.
CPC ............ *A61K 31/295* (2013.01); *A61K 9/143* (2013.01); *A61K 31/555* (2013.01); *A61K 33/26* (2013.01)

(58) Field of Classification Search
None
See application file for complete search history.

(56) References Cited

U.S. PATENT DOCUMENTS

| | | | | |
|---|---|---|---|---|
| 5,753,706 A | * | 5/1998 | Hsu ...................... | A61K 31/295 514/578 |
| 8,299,298 B2 | * | 10/2012 | Chan .................... | A61K 31/295 562/582 |
| 8,754,257 B2 | * | 6/2014 | Chan .................... | A61K 31/295 562/582 |
| 9,050,316 B2 | * | 6/2015 | Chan .................... | A61K 31/295 |
| 9,750,715 B2 | * | 9/2017 | Chan .................... | A61K 31/295 |
| 9,757,416 B2 | * | 9/2017 | Chan ...................... | A61K 33/26 |
| 2006/0020026 A1 | * | 1/2006 | Kwok .................. | A61K 31/295 514/502 |

* cited by examiner

Primary Examiner — Svetlana M Ivanova
(74) Attorney, Agent, or Firm — Law Offices of Albert Wai-Kit Chan, PLLC

(57) ABSTRACT

The present invention provides methods of treating soft tissue calcification in a subject, comprising a step of administering to said subject an effective amount of ferric organic compound, such as ferric citrate. The claimed methods may prevent, reverse, delay or stabilize soft tissue calcification in a subject having chronic kidney disease. Affected soft tissue calcification includes soft tissue calcification in the joint, skin, eye, in cardiovascular system such as heart valve, myocardium, coronary arteries and arteriole, or in internal organs such as kidney and lung.

13 Claims, 9 Drawing Sheets

Figure 2

| | Pharmaceutical grade Ferric Citrate Phase II Clinical Study 2005 | | | | | | | | Chemical grade Ferric Citrate Clinical Study in Taiwan 1998 | | Chemical grade Ferric Citrate Clinical Study in U.S 1998 | |
|---|---|---|---|---|---|---|---|---|---|---|---|---|
| | Placebo (N=16) | | Ferric Citrate 2g/day (N=33) | | Ferric Citrate 4g/day (N=34) | | Ferric Citrate 6g/day (N=33) | | Ferric Citrate 3g/day (N=45) | | Ferric Citrate 4.5g/day (N=14) | |
| | # Event | % | # Event | % | # Event | % | # Event | % | # Event | % | # Event | % |
| Diarrhea | 2 | 12.5% | 3 | 9.1% | 1 | 2.9% | 1 | 3.0% | 9 | 20.0% | 3 | 21.4% |
| Loose stool | 1 | 6.3% | 0 | 0.0% | 1 | 2.9% | 1 | 3.0% | 3 | 6.7% | 5 | 35.7% |
| Constipation | 0 | 0.0% | 0 | 0.0% | 2 | 5.9% | 1 | 3.0% | 4 | 8.9% | 1 | 7.1% |
| Bloating | 1 | 6.3% | 0 | 0.0% | 0 | 0.0% | 1 | 3.0% | 5 | 11.1% | 3 | 21.4% |
| Nausea | 0 | 0.0% | 2 | 6.1% | 0 | 0.0% | 1 | 3.0% | 0 | 0.0% | 0 | 0.0% |

Figure 3

Serum phosphorus (mg/dl)

| | Pharmaceutical grade Ferric Citrate Clinical Study 2005 | | | | Chemical grade Ferric Citrate Clinical Study in Taiwan 1998 | Chemical grade Ferric Citrate Clinical Study in U.S 1998 |
|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 4.5g/day (N=14) |
| Day 0 (Baseline) | 7.2±1.4 | 7.2±1.2 | 7.1±1.3 | 7.3±1.3 | 6.7±1.9 | 7.2±2.5 |
| Day 28 (End of treatment) | 7.2±1.2 | 6.9±2.2 | 6.0±1.3 | 5.8±1.8 | 5.7±1.6 | 5.9±2.0 |
| Difference from baseline | -0.1±2.0 | -0.3±2.1 | -1.1±1.6 | -1.5±1.6 | -1.0±2.5 | -1.3±3.2 |

[Ca]×[P] (mg/dl)$^2$

| | Pharmaceutical grade Ferric Citrate Clinical Study 2005 | | | | Chemical grade Ferric Citrate Clinical Study in Taiwan 1998 | Chemical grade Ferric Citrate Clinical Study in U.S 1998 |
|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 4.5g/day (N=14) |
| Day 0 (Baseline) | 62.8±14.0 | 62.9±13.3 | 63.5±10.7 | 65.8±12.2 | 60.8±17.1 | 60.3±15.5 |
| Day 28 (End of treatment) | 63.2±12.6 | 61.7±21.3 | 55.4±13.4 | 54.1±17.7 | 51.8±15.2 | 51.8±17.7 |
| Difference from baseline | -0.3±19.3 | -1.1±20.7 | -8.1±14.7 | -11.7±15.4 | -9.0±22.9 | -8.5±23.5 |

Figure 9
| | 1st Examination | 2nd Examination |
|---|---|---|
| Inner side | 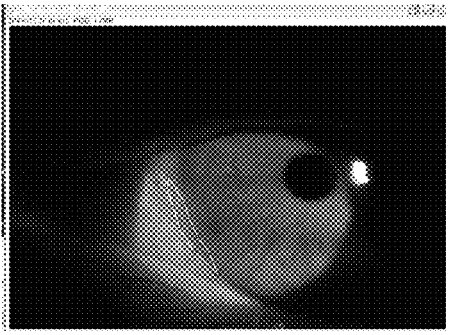 | 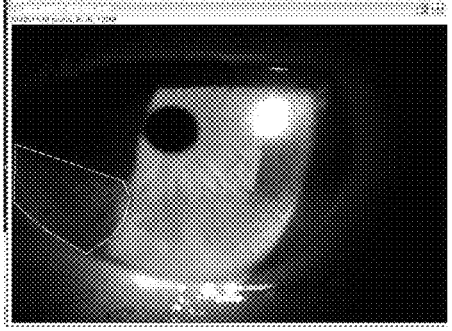 |
| Outer side | 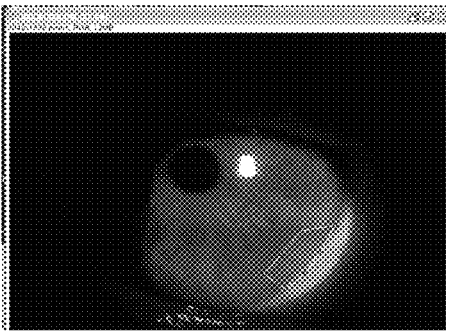 | 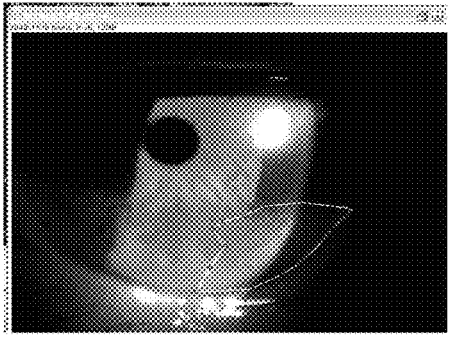 |
| Results | 1st Examination on right eye<br>Cornea calcification (%):<br>Inner side: + 1.64%<br>Outer side: + 2.68%<br><br>Total: + 4.32% | 2nd Examination on right eye<br>Cornea calcification (%):<br>Inner side: + 8.20%<br>Outer side: + 7.93%<br><br>Total: + 16.13% |
| | Difference (2nd – 1st) = + 11.81% | |

Figure 10
| | 1st Examination | 2nd Examination |
|---|---|---|
| Inner side | 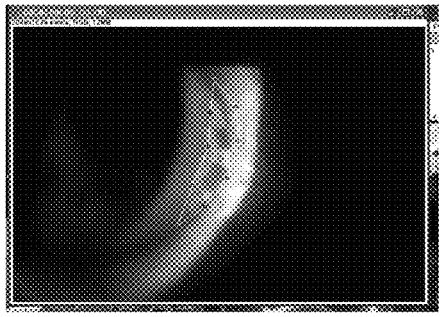 |  |
| Outer side | 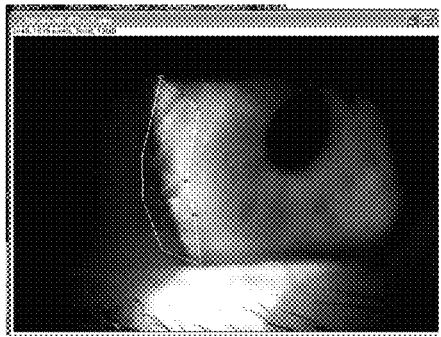 | 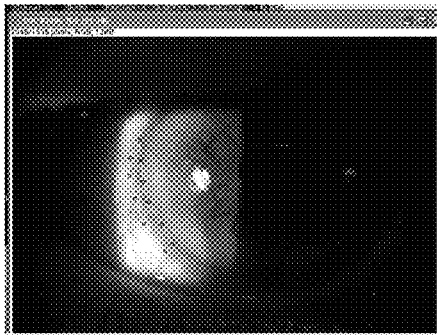 |
| Results | 1st Examination on right eye<br>Cornea calcification (%):<br>Inner side: −6.59%<br>Outer side: −8.31%<br><br>Total: −14.9% | 2nd Examination on right eye<br>Cornea calcification (%):<br>Inner side: −2.19%<br>Outer side: −2.50%<br><br>Total: −4.69% |
| | Difference (2nd − 1st) = −10.21% | |

METHOD FOR REVERSING, PREVENTING, DELAYING OR STABILIZING SOFT TISSUE CALCIFICATION

This application claims priority of U.S. provisional application No. 60/763,253, filed Jan. 30, 2006, and PCT/US2006/032385, filed Aug. 18, 2006. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

BACKGROUND OF THE INVENTION

It is estimated that 1 in 9 individuals in the United States have some manifestation of chronic kidney disease (CKD), ranging from proteinuria with normal renal clearance/function to advanced renal failure requiring renal replacement therapy in the form of dialysis or transplantation, commonly called end-stage renal disease (ESRD). The American Heart Association recently published a Scientific Statement that details strong evidence supporting that individuals with chronic kidney disease should be included in the highest-risk group for cardiovascular disease and therefore should receive aggressive preventive measures to reduce the prevalence and severity of cardiovascular disease.

Cardiovascular mortality is the leading cause of death in patients treated by dialysis, with mortality 10 to 30 times higher than the general population despite stratification for sex, race, and presence of diabetes. Similarly, cardiovascular mortality is 2 to 5 times higher than the general population in patients with a functioning renal transplant. This is likely from (1) the extremely high prevalence of atherosclerosis, heart failure, and left ventricular failure in hemodialysis patients, observed in 40% to 74% of incident dialysis patients and (2) a high case mortality rate after an acute myocardial infarct or of heart failure.

Coronary artery calcification is very common in dialysis patients. Depending on the age of the patient population examined, 54% to 100% (mean 83%) of dialysis patients in case series have some degree of coronary artery calcification, with scores markedly above the general population. Coronary artery calcification is also present in adolescents and young adults with chronic kidney disease. Once coronary artery calcification is present in dialysis patients, it is rapidly progressive in nearly all studies, with minimal or no progression after renal transplantation.

Under normal physiological condition, serum calcium and phosphorous are tightly controlled and balanced. However, the degenerated kidney in renal disease patients will fail to adequately response to regulation system and decrease phosphorus excretion. With the worsening of kidney condition and phosphorus accumulation, parathyroid will continuously increase production of parathyroid hormone (PTH). High PTH induces calcium release from bone to serum. As a result, most of the patients with renal failure will be found to have elevated serum phosphorus, calcium and PTH. Hyperphosphatemia, increased Calcium and Phosphorus (CaxP) product in serum, hyperparathyroidism and increased calcium intake have been considered as significant predictors of cardiovascular morbidity and mortality, potentially acting as progression factors of unwanted calcifications in uremia (Block and Port (2000), Re-evaluation of risks associated with hyperphosphatemia and hyperparathyroidism in dialysis patients: recommendations for a change in management. American Journal of Kidney Diseases, 35:1226-1237; Ketteler et al. (2005), Pathogenesis of vascular calcification in dialysis patients. Clin. Exp. 9:265-270).

Phosphorous exerts a negative impact on vascular calcification by direct participation in the change of CaxP and indirectly in the pathogenesis and progression of hyperthyroidism. Serum calcium and phosphorous are metastable under normal circumstances, which means that their concentrations are not sufficient to produce spontaneous precipitation. However, once the calcification process begins, the concentrations are sufficient to support crystal proliferation.

It is believed that the abnormally high calcium and phosphorus concentration contribute to randomly passive precipitation of calcium phosphate in body. Although the whole mechanism of action is still under exploration, recent studies have found a more complicated and active pathway that the disturbances of mineral metabolism (hyperphosphatemia and hypercalcemia) appear to further induce genetic changes in vascular smooth muscle cell and change the cell behavior toward an osteoblast-like phenotype contributing to progressive calcification (Ketteler et al. (2005), Pathogenesis of vascular calcification in dialysis patients. Clin. Exp. 9:265-270).

The degree of abnormal soft-tissue calcification progressed as degree of renal disease increased and can happen through out the body in organs such as skin, joint, eye, heart valve, myocardium, coronary arteries, arterioles, lung, kidney, etc. Among them, ocular calcification is among the most frequently observed and highly prevalent soft-tissue calcification in hemodialysis patients (Tilman Drueke and Isidro Salusky, The Spectrum of Renal Osteodystrophy. Oxford University Press. p345-357). Ectopic calcifications mostly occurs on the limbal area exposed by the interpalpebral fissure on conjunctiva and cornea, and appear as fine white deposits, coarse granular crystals, or flatter plaques. If not well managed, calcification on the eye area may lead to decrease of vision, irritation and ocular discomfort which may worsen to the point of becoming disabling. In addition, calcium deposits may cause epithelial and persistent tissue defects.

A recent study further investigated the relationship between the severity of eye calcification and occurrence of vascular calcification in dialysis patients and found a significant correlation between the degree of ocular calcification and status of extra-skeletal calcification. The study suggested the degree of ocular calcification may be used as a tool to assess the status of extra-skeletal calcification such as soft tissue calcification or any other organ calcifications (Seyahi et al. (2005), Association of conjunctival and corneal calcification with vascular calcification in dialysis patients. American Journal of Kidney Disease 45:550-556).

The development of calcification in cardiovascular system can lead to development of a number of clinically significant complications such as myocardial ischemia, myocardial infarction, impaired myocardial function, congestive heart failure and cardiac valve insufficiency. The accelerated development of cardiovascular disease, particularly coronary artery disease and chronic heart failure, is the leading cause of death in patients with end stage renal disease. It has been reported that the yearly all-cause mortality in dialysis patients ranges between 12% and 25%. Among them approximately 50% of this excess mortality is due to cardiovascular causes (Ketteler et al., 2005).

Calcification also extends beyond renal disease patients and can include anyone who is over the age of 40. While the leading cause of death in the United States is acute myocardial infarction and stroke, hypercholesteromia contribute to only 15% of the deaths in this category and 85% is caused by ventricular calcification.

Accordingly, there exists a need for a method of managing or reducing serum phosphorous, Calcium and Phosphorus product (CaxP) and parathyroid hormone (PTH) levels in subjects that have an increased risk of developing vascular, visceral or soft tissue calcification. The present invention provides methods of using novel forms of ferric organic compounds that satisfy this need.

SUMMARY OF THE INVENTION

In accordance with these and other objects of the invention, a brief summary of the invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention provides a method of treating soft tissue calcification in a subject, comprising administering to said subject an effective amount of a ferric organic compound. In one embodiment, the ferric organic compound has a dissolution rate of at least approximately 2 $mg/cm^2/min$.

In one embodiment, the ferric organic compound is made according to a method comprising the steps of: (a) obtaining a ferric iron salt; (b) adding an alkaline metal hydroxide to the ferric iron salt under conditions effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by an organic solvent.

In general, a subject is a human or an animal. The subject may have chronic kidney disease or end stage renal disease, is undergoing renal dialysis or renal transplantation. The ferric organic compound may be administered orally or any other appropriate route generally known in the art. An effective amount of the ferric organic compound can be readily determined by one of ordinary skill in the art, and the ferric organic compound can be formulated into a number of formats generally known in the art. Representative formats include, but are not limited to, a tablet, a powder, a suspension, an emulsion, a capsule, a lozenge, a granule, a troche, a pill, a liquid, a spirit, or a syrup.

In one embodiment, treatment with the ferric organic compound may prevent, reverse, delay, or stabilize soft tissue calcification in the subject, wherein the soft tissues include, but are not limited to, soft tissue in skin, joints, eye, heart valve, myocardium, coronary arteries, lung, kidney, etc.

The present invention also provides a therapeutic regimen for treating soft tissue calcification in a subject, the regiment comprises a pharmaceutical composition comprising an acceptable carrier and an effective amount of ferric organic compound, wherein the pharmaceutical composition is administered in single or multiple doses regimens. In one embodiment, the ferric organic compound has a dissolution rate of at least approximately 2 $mg/cm^2/min$. An example of ferric organic compound is ferric citrate.

The present invention also provides a pharmaceutical composition for treating soft tissue calcification in a subject, the composition comprising an effective amount of a ferric organic compound having a dissolution rate of at least approximately 2 $mg/cm^2/min$. In general, the pharmaceutical composition can be formulated as a tablet, a powder, a suspension, an emulsion, a capsule, a lozenge, a granule, a troche, a pill, a liquid, a spirit, or a syrup.

The present invention also provides uses of a pharmaceutical composition comprising an effective amount of ferric organic compound in preparation of a medicament for treating soft tissue calcification in a subject. In one embodiment, the ferric organic compound (e.g. ferric citrate) has a dissolution rate of at least approximately 2 $mg/cm^2/min$.

Other advantages and aspects of the present invention will become apparent upon reading the following examples.

DETAILED DESCRIPTION OF THE FIGURES

FIG. 2 is a comparison of the safety profiles of chemical grade and pharmaceutical grade ferric citrates FIG. 3 is a comparison of the efficacy profiles of chemical grade and pharmaceutical grade ferric citrates

FIG. 9 shows an example of worsened cornea calcification in a patient without ferric citrate treatment. Patient ID: 2-01-001; dose: placebo; treatment period: 77 days.

FIG. 10 shows an example of improved cornea calcification in a patient after ferric citrate treatment. Patient ID: 2-01-1-012; dose: ferric citrate 2 g/day; treatment period: 28 days.

DETAILED DESCRIPTION OF THE INVENTION

Figure 1:
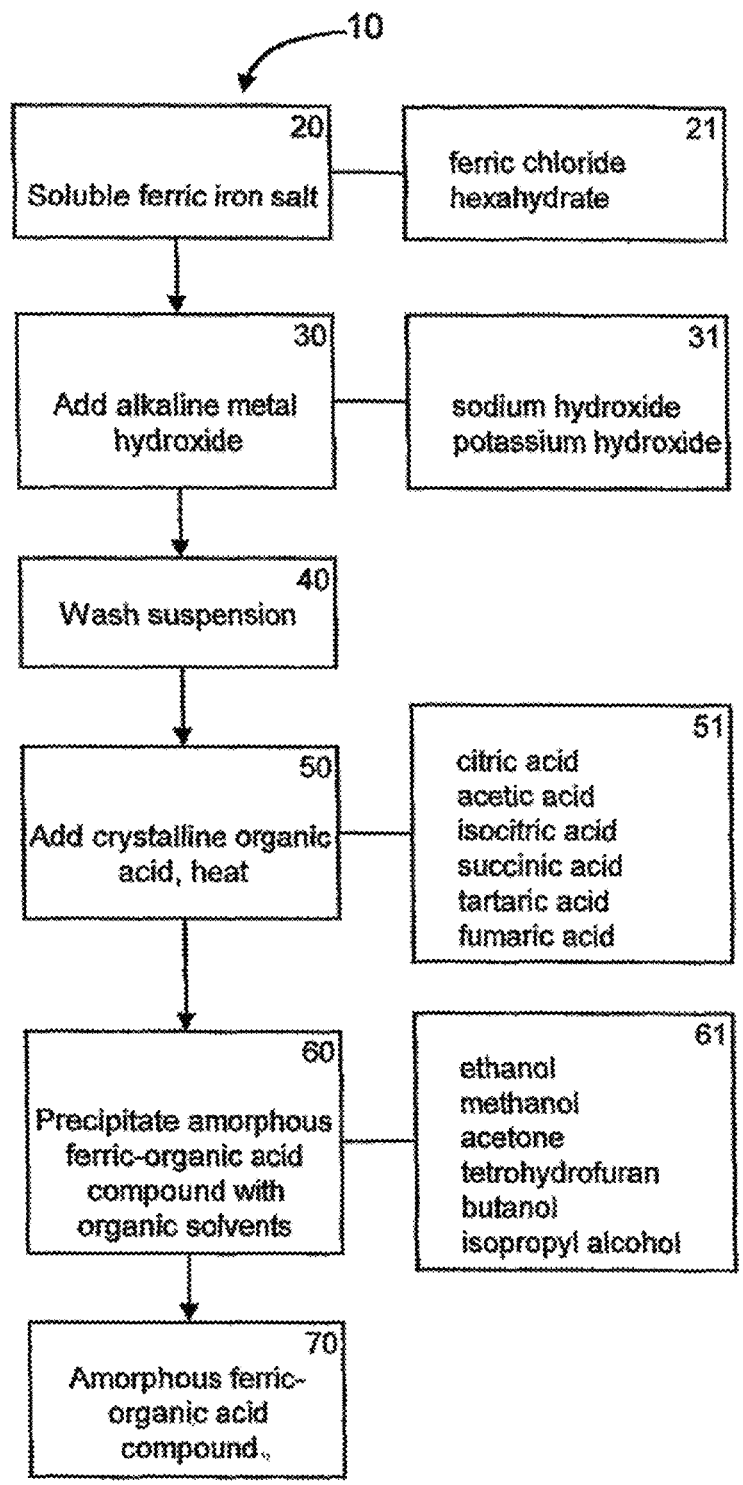
FIG. 1 is a schematic diagram outlining the method of making novel forms of ferric organic compounds according to the present invention.

Methods of making novel ferric organic compounds, such as ferric citrate, have been disclosed in U.S. provisional application No. 60/763,253, and PCT/US2006/032585, which are hereby incorporated by reference in their entireties. These ferric compounds are more soluble in a wider range of pH than commercially available forms of ferric citrate compounds or complexes. Furthermore, the ferric organic compounds of the present invention have a larger active surface area as compared to commercially available forms of ferric citrate compounds. Because these ferric organic compounds are more soluble, they can be more effectively delivered orally to patients suffering from conditions which are responsive to treatment with ferric organic compounds such as ferric citrate.

Results presented below suggest that treatment with ferric citrate of the present invention may delay or improve visceral, vascular and/or soft tissue calcification such as cornea calcification. Hence, an effective amount of the ferric citrate can be used to reverse, prevent, delay, or stabilize visceral, vascular and/or soft tissue calcification in a subject.

The present invention is not limited to using the ferric citrate disclosed herein. Other ferric citrate compounds, or their salts, derivatives, analogs, metabolites, or preparations that are suitable for use in the methods of the present invention will be readily apparent to a person of ordinary skill in the art by following the teaching of this application. Furthermore, methods of the present invention also encompass using other ferric organic compounds synthesized according to the methods described herein. These ferric organic compounds preferably have or include the following properties:

high affinity for binding phosphorous;
soluble over a wide range of pH;
rapid binding independent of pH;
high solubility;
low absorption throughout the entire body;
lack of toxicity;
can be administered orally; and/or
inexpensive to produce.

In view of the data presented herein, one of ordinary skill in the art would also readily realize that the present invention is not limited to using ferric organic compounds produced according to the method disclosed herein. Hence, it will be readily apparent to a person of ordinary skill in the art that the present invention encompasses methods of using ferric organic compounds to treat soft tissue calcification, wherein the ferric organic compounds possess certain characteristics as described herein.

In one embodiment, methods of the present invention comprise administering to a subject an effective amount of a ferric organic compound and a suitable carrier. As used herein, the term "suitable carrier" includes, but is not limited to, any suitable carrier for administering pharmaceutical compounds or compositions known to those of ordinary skill in the art. The type of carrier will vary depending on the mode of administration. An "acceptable or suitable carrier" may also include, but is not limited to, a liquid, an aerosol, a capsule, a tablet, a pill, a powder, a gel, an ointment, a cream, a granule, water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells or cellular membranes. Biodegradable microspheres (e.g., polylactate polyglycolate) may also be employed as carriers.

With regards to compounds or compositions for parenteral administration (e.g. subcutaneous injections), the term suitable carrier includes, but is not limited to, water, saline, alcohol, a fat, a wax or a buffer.

With regards to compounds or compositions for oral administration, the term suitable carrier includes, but is not limited to, any of the above carriers or a solid carrier, such as mannitol, lactose, starch, magnesium stearate, sodium saccharine, talcum, cellulose, glucose, sucrose, and magnesium carbonate.

In one embodiment, the present invention provides a method of using ferric organic compound to treat soft tissue calcification in a subject. In general, the subject is a human or an animal. The subject may have chronic kidney disease, or end stage renal disease, or is undergoing renal dialysis. The ferric organic compound is synthesized as described herein. Briefly, the synthetic method comprises the steps of:
(a) obtaining a ferric iron salt (e.g. ferric chloride hexahydrate); (b) adding an alkaline metal hydroxide (e.g. sodium hydroxide) to the ferric iron salt at a rate and temperature effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by an organic solvent.

The present invention also provides a method of treating soft tissue calcification in a subject, comprising administering to said subject an effective amount of a ferric organic compound. In general, the ferric organic compound has a dissolution rate of at least approximately 2 mg/cm$^2$/min., e.g. from about 2 mg/cm$^2$/min. to about 4 mg/cm/min.

In one embodiment, the ferric organic compound is made according to a method comprising the steps of: (a) obtaining a ferric iron salt; (b) adding an alkaline metal hydroxide to the ferric iron salt under conditions effective to produce a mixture comprising polyiron oxide; (c) isolating a precipitate from the mixture; (d) adding an organic acid to the precipitate; (e) forming a ferric organic acid solution by heating the organic acid and the precipitate; and (f) precipitating the ferric organic compound from the ferric organic acid solution by an organic solvent.

In one embodiment, the alkaline metal hydroxide is added at a rate of less than 20 ml/min, preferably between about 10 ml/min to about 20 ml/min., and the alkaline metal hydroxide is added to the ferric iron salt at a temperature of less than 40° C., preferably between about 10° C. to about 40° C.

In one embodiment, the organic acid and the precipitate are heated to a temperature of between about 80° C. to about 90° C. Precipitating the ferric organic compound from the ferric organic acid solution by adding an organic solvent to the solution comprises cooling the ferric organic acid solution to less than 30° C. before adding the organic solvent, preferably the ferric organic acid solution is cooled to a temperature between about 10° C. to about 30° C.

A number of organic acids, such as citric acid, acetic acid, isocitric acid, succinic acid, fumaric acid, and tartaric acid can be used in the method of synthesizing the ferric organic compound, whereas a number of organic solvent, such as ethanol, methanol, butanol, isopropyl alcohol, acetone, and tetrahydrofuran can be used.

The ferric organic compound can be administered at an effective dose determined by one of ordinary skill in the art. For example, the effective amount of the ferric organic compounds may be determined by titration experiments in animal or appropriate in vitro model. Examples of effective amount include, but are not limited to, 2-8 gm/day of ferric organic compound administered three times a day, 6 gm/day for 14 days or 28 days, or the ferric organic compound is administered equally three times a day, or the ferric organic compound is administered within 10 minutes after meal.

Even though different routes of administration, such as i.v., i.p. or intradermal delivery, may work the same, or may be as effective, the ferric organic compounds of the present invention are preferably administered orally. In general, the ferric organic compound can be formulated as a tablet, a powder, a suspension, an emulsion, a capsule, a lozenge, a granule, a troche, a pill, a liquid, a spirit, or a syrup.

In one embodiment, treatment with the ferric organic compound may prevent, reverse, delay or stabilize soft tissue calcification in the subject, wherein the soft tissues include, but are not limited to, soft tissue in the skin, joint, eye, heart valve, myocardium, coronary arteries, arterioles, or in internal organs such as lung and kidney.

The present invention also provides a therapeutic regimen for treating soft tissue calcification in a subject, the regiment comprises a pharmaceutical composition comprising an acceptable carrier and an effective amount of ferric organic compound, wherein the pharmaceutical composition is administered in single or multiple doses regimens. In one embodiment, the ferric organic compound has a dissolution rate of at least approximately 2 mg/cm$^2$/min. An example of ferric organic compound is ferric citrate.

In general, at least a portion of the pharmaceutical composition is administered orally, e.g. the ferric organic compound can be formulated as a tablet, a powder, a suspension, an emulsion, a capsule, a lozenge, a granule, a troche, a pill, a liquid, a spirit, or a syrup. The therapeutic regimen is useful for treating a subject with chronic kidney disease or end stage renal disease. In one embodiment, treatment with the therapeutic regimen may prevent, reverse, delay, or stabilize soft tissue calcification in the subject, wherein the soft tissues include, but are not limited to, soft tissue in the skin, joint, eye, heart valve, myocardium, coronary arteries, arterioles, or in internal organs such as lung and kidney The present invention also provides a pharmaceutical composition for treating soft tissue calcification in a subject, the composition comprising an effective amount of a ferric organic compound having a dissolution rate of at least approximately 2 mg/cm$^2$/min., e.g. from about 2 mg/cm$^2$/min. to about 4 mg/cm$^2$/min. The pharmaceutical composition can be formulated into various forms as described above, and it is useful for treating soft tissue calcification as described above.

The present invention also provides a use of a pharmaceutical composition comprising an effective amount of ferric organic compound in preparation of a medicament for treating soft tissue calcification in a subject. In one embodiment, the ferric organic compound (such as ferric citrate) has a dissolution rate of at least approximately 2 mg/cm$^2$/min. The resulting medicament can be formulated into various forms as described above, and it is useful for treating soft tissue calcification as described above.

The invention being generally described, will be more readily understood by reference to the following examples which are included merely for purposes of illustration of certain aspects and embodiments of the present invention, and are not intended to limit the invention.

Example 1

General Method for Synthesis of a Pharmaceutical-Grade Ferric Organic Compound

General methods for the synthesis of ferric organic compounds have been disclosed in PCT/US2006/032585, and U.S. provisional application No. 60/763,253, which are incorporated by reference into this application. Representative ferric organic compounds include, but are not limited to, ferric citrate.

Referring to FIG. 1, the flowchart 10 is a general process for synthesizing a form of ferric organic compound or ferric citrate compound which can be used in the present invention. The starting materials, as indicated in box 20, comprise soluble ferric iron salts. The soluble ferric iron salts can comprise ferric chloride hexahydrate (FeCl$_3$6H$_2$O), as indicated in box 21, or any other suitable soluble ferric iron salt. Next, an alkaline metal hydroxide (box 30) is added at a specific rate and temperature to the soluble ferric iron salt. The addition of the alkaline metal hydroxide at a specific rate, preferably between about 10 ml/min and about 20 ml/min, and temperature range, preferably below 40° C., results in the formation of a uniform polyiron oxo colloidal suspension. The alkaline metal hydroxide can comprise sodium hydroxide, potassium hydroxide, or any other suitable alkaline metal hydroxide as indicated in box 31.

The colloidal suspension precipitate is collected and rinsed (box 40) with distilled water to remove any soluble impurities. After rinsing, the precipitate is re-suspended and, as indicated in box 50, crystalline organic acid is added to the precipitate and heated to a particular temperature range, preferably between about 80° C. to about 90° C. The organic acid can comprise any suitable organic acid. Box 51 lists some of the possible organic acids which can be used, including, but not limited to, citric acid, acetic acid, isocitric acid, succinic acid, fumaric acid, and tartaric acid. The addition of the organic acid allows the acid to form complexes with the precipitate in solution. At box 60, the ferric organic compound is precipitated out of solution with an organic solvent to form a novel form of ferric organic compound (box 70). Various organic solvents can be used, including, but not limited to, the solvents described in box 61, such as ethanol, methanol, butanol, acetone, isopropyl alcohol, tetrahydrofuran, or any other suitable organic solvent.

Synthesis of Ferric Citrate

In one embodiment of the invention, the ferric organic compound is ferric citrate. The starting materials for making a ferric citrate comprise a 1.85M solution of ferric chloride hexahydrate (FeCl$_3$6H$_2$O). A volume of 5M sodium hydroxide necessary to produce a 1:3 ratio of ferric iron to hydroxide ion is added to the ferric chloride hexahydrate solution at a rate of less than 20 ml per minute, preferably between about 10 ml per minute and about 20 ml per minute. The temperature of the mixture is maintained below 40° C., preferably between about 10° C. to about 40° C., while the sodium hydroxide is added to form a polyiron oxide colloidal suspension of ferric hydroxide. The pH of the suspension is measured while the sodium hydroxide is added. Once the pH is above 7.0, the suspension is cooled until it is less than 30° C., preferably between about 10° C. to about 30° C. The suspension is then filtered through a 1 mm pore filter to breakup aggregates and large particles of ferric hydroxide precipitate are then removed. The filtered ferric hydroxide suspension is then centrifuged. The supernatant is discarded, and the precipitated ferric hydroxide is centrifuged again to remove any remaining supernatant. The ferric hydroxide precipitate is then resuspended with distilled water. The centrifugation-resuspension steps are repeated two more times to wash the ferric hydroxide precipitate and remove water soluble impurities. The resulting ferric hydroxide precipitate is then homogenized.

An amount of citric acid necessary to produce a 1:1 ratio of ferric iron to citrate is added to the precipitate. The mixture is heated to between about 80° C. to about 90° C. in an oil bath until the color of the mixture changes from orange-brown to a clear black-brown, or until all of the ferric hydroxide precipitate is dissolved. The reaction is cooled until it is less than 30° C., preferably between about 10° C. to about 30° C., and the pH is measured to determine that it is within 0.8 and 1.5. The reaction is centrifuged, and the supernatant is collected. Ferric citrate is precipitated from the supernatant by adding 5 volumes of organic solvent.

Various organic solvents can be used, including ethanol, methanol, butanol, acetone, isopropyl alcohol, or tetrahydrofuran. Once the solvent is added, the mixture is stirred until a light beige precipitate forms. The suspension is centrifuged and the supernatant is discarded. The precipitate is washed and centrifuged with the solvent two more times. The precipitate is then dried in a vacuum oven for 8 to 16 hours at ambient temperature or by any other suitable industrial processes such as fluidized-bed drying. The dried precipitate is ground with a mortar and pestle and dried for another 8 to 24 hours at ambient temperature. The fine precipitate is finely ground by milling again and screened through a 45 mesh size (35 micron) sieve. The novel form of ferric citrate powder is dried in the vacuum oven again or fluidized-bed drying again and dried at ambient temperature until 1 hour of drying leads to less than 0.25% loss in weight.

Example 2

Randomized, Double-Blind, Placebo-Controlled, Dose-Ranging Study of the Effects of Ferric Citrate on Serum Phosphate in Patients with End Stage Renal Disease (ESRD)

Objectives: (1) To determine the effect of ferric citrate at doses of 2, 4 and 6 g daily, administered TID (three times a day), for 28 days on serum phosphate (PO4) levels in patients with end stage renal disease (ESRD). (2) To evaluate the safety of ferric citrate at doses of 2, 4, 6 g daily, administered TID, for 28 days in patients with ESRD.

Study Drug: Ferric citrate disclosed in U.S. Ser. No. 11/206,981 and WO 2004/07444.

Study Design: Randomized, double-blind, placebo-controlled, dose-ranging study to assess the effect of ferric citrate on serum phosphate concentrations in patients with ESRD on hemodialysis. Patients are assessed at Study Days 14 and 28 for effectiveness as measured by serum phosphate concentrations. Patients who received one or more doses of study medication are also assessed for safety.

Study Duration: 8 weeks (including the screening period, 2 weeks washout, 4 weeks treatment)

Results show a decrease in serum PO4 and Ca*PO4 at 0, 2, 4 and 6 gm/day (given as TID immediately after meals, i.e., within 10 minutes). Ferric citrate is administered orally, and is given equally three times a day.

The ability of ferric citrate to lower the serum phosphate levels in patients with ESRD was demonstrated. No significant change was observed in the serum calcium level during the 28 days for placebo, 2, 4, and 6 gm/day. However, the Ca*PO4 levels have decreased and were statistically significant for 6 gm/day dose at both 14 and 28 days. The results also indicate that calcification may be reversed or stabilized following treatment with ferric citrate. The Tables below summarize the data the study.

TABLE 1

Summary of Results

| | Dose Response | Statistical Significant | Linear Regression |
|---|---|---|---|
| Serum PO4 (mg/dL) | | | |
| Day 14 | No | No | P = 0.0523 |
| Day 28 | Yes | Yes (6 g/day) | P = 0.0073 |
| Serum Ca (mg/dL) | | | |
| Day 14 | No | No | N.S. |
| Day 28 | No | No | N.S. |
| Ca × PO4 (mg/dL)$^2$ | | | |
| Day 14 | Yes | No | P = 0.0401 |
| Day 78 | Yes | Yes (6 g/day) | P = 0.0158 |

* N.S.: Not Significant

TABLE 2

Summary of Serum [PO4] (mg/dL)

| | Placebo (N = 16) | 2 g/day (N = 31) | 4 g/day (N = 32) | 6 g/day (N = 32) | Dose Response |
|---|---|---|---|---|---|
| Serum [PO4] (mg/dL) at Day 0 | 7.2 ± 1.43 | 7.2 ± 1.23 | 7.1 ± 1.27 | 7.3 ± 1.33 | N/A |
| Serum [PO4] (mg/dL) at Day 14 | 6.7 ± 1.22 | 6.7 ± 1.50 | 6.4 ± 1.56 | 6.3 ± 1.72 | No (P = 0.0523) |
| Serum [PO4] (mg/dL) at Day 28 | 7.2 ± 1.19 | 6.9 ± 2.22 | 6.0 ± 1.33 | 5.8 ± 1.76* | Yes |

*P < 0.05, Significant Difference Baseline Change as Compared to Placebo

TABLE 3

Summary of Serum [Ca] (mg/dL)

| | Placebo (N = 16) | 2 g/day (N = 31) | 4 g/day (N = 32) | 6 g/day (N = 32) | Dose Response |
|---|---|---|---|---|---|
| Serum [Ca] (mg/dL) at Day 0 | 8.71 ± 0.779 | 8.78 ± 0.981 | 9.02 ± 0.913 | 8.99 ± 0.812 | No |
| Serum [Ca] (mg/dL) at Day 14 | 8.91 ± 0.782 | 9.01 ± 1.232 | 9.47 ± 0.990 | 9.13 ± 0.909 | No |
| Serum [Ca] (mg/dL) at Day 28 | 8.74 ± 0.830 | 9.00 ± 0.953 | 9.29 ± 0.960 | 9.26 ± 0.865 | No |

* P < 0.05, Significant Difference Baseline Change as Compared to Placebo

TABLE 4

Summary of Serum [Ca] * [PO4] (mg/dL)$^2$

| | Placebo (N = 16) | 2 g/day (N = 31) | 4 g/day (N = 32) | 6 g/day (N = 32) | Dose Response |
|---|---|---|---|---|---|
| [Ca] * [PO4] (mg/dL)$^2$ at Day 0 | 62.8 ± 13.91 | 62.9 ± 13.25 | 63.5 ± 10.69 | 65.8 ± 12.19 | N/A |
| [Ca] * [PO4] (mg/dL)$^2$ at Day 14 | 59.9 ± 12.19 | 60.3 ± 16.50 | 59.9 ± 13.89 | 57.5 ± 16.27 | Yes |
| [Ca] * [PO4] (mg/dL)$^2$ at Day 28 | 63.2 ± 12.55 | 61.7 ± 21.25 | 55.4 ± 13.36 | 54.1 ± 17.68* | Yes |

*P < 0.05, Significant Difference Baseline Change as Compared to Placebo

TABLE 5

| Treatment-Emergent Adverse Events | | | | |
|---|---|---|---|---|
| | Placebo (N = 16) # Event (%) | 2 g/day (N = 33) # Event (%) | 4 g/day (N = 34) # Event (%) | 6 g/day (N = 33) # Event (%) |
| Total number of subjects with at least one adverse event (T#at1AE) Sorted by Preferred Term (PT) | 7 (43.8) | 16 (48.5) | 12 (35.3) | 17 (51.5) |
| Abdominal Pain | 0 (0.0) | 0 (0.0) | 4 (11.8) | 2 (6.1) |
| Diarrhea | 2 (12.5) | 3 (9.1) | 1 (2.9) | 1 (3.0) |
| Sorted by System Organ Class/PT | | | | |
| GI Disorders (see above PT) | 4 (25.0) | 8 (24.2) | 10 (29.4) | 10 (30.3) |
| General Disorders | 2 (12.5) | 4 (12.1) | 2 (5.9) | 4 (12.1) |
| Infections and Infestations | 2 (12.5) | 0 (0.0) | 3 (8.8) | 1 (3.0) |
| Skin and SC Tissue Disorders | 0 (0.0) | 3 (9.1) | 0 (0.0) | 4 (12.1) |
| Sorted by SOC/PT/Severity | | | | |
| T#at1AE, Mild | 7 (43.8) | 13 (39.4) | 9 (26.5) | 14 (42.4) |
| T#at1AE, Moderate | 0 (0.0) | 6 (18.2) | 3 (8.8) | 2 (6.1) |
| T#at1AE, Severe | 1 (6.3) | 0 (0.0) | 2 (5.9) | 1 (3.0) |
| GI Disorders, Mild | 4 (25.0) | 6 (18.2) | 8 (23.5) | 9 (27.3) |
| Sorted by SOC/PT/Relationship | | | | |
| T#at1AE, Definitely | 0 (0.0) | 0 (0.0) | 0 (0.0) | 0 (0.0) |
| T#at1AE, Probably | 1 (6.3) | 2 (6.1) | 2 (5.9) | 5 (15.2) |
| T#at1AE, Possibly | 3 (18.8) | 5 (15.2) | 6 (17.6) | 2 (6.1) |
| GI Disorder, Definitely | 0 (0.0) | 0 (0.0) | 0 (0.0) | 0 (0.0) |
| GI Disorder, Probably | 1 (6.3) | 2 (6.1) | 2 (5.9) | 5 (15.2) |
| GI Disorder, Possibly | 3 (18.8) | 3 (9.1) | 6 (17.6) | 1 (3.0) |

As shown in FIGS. 2 and 3, treatments using pharmaceutical-grade ferric citrate provide several advantages over chemical grade ferric citrate. In general, while pharmaceutical-grade ferric citrate demonstrates an efficacy approximately equal to that of chemical grade ferric citrate, it achieves this result with less adverse side effects than chemical grade ferric citrate.

FIG. 2 also indicates that adverse side effects associated with administering pharmaceutical-grade ferric citrate were not statistically different from those associated with the placebo. An advantage of this safety profile is that an individual patient may have his dosing of pharmaceutical-grade ferric citrate titrated over a broad range of doses with less concern about side effect. In this way, a patient's individual treatment may be tailored to suit his specific needs and tolerances. Decrease in Serum Creatinine Level Glomerular filtration rate (GFR) level correlates with structural kidney damage and is used as a golden standard to measure kidney function. GFR can be estimated by the biomarkers serum creatinine. As renal function deteriorates, kidney lost its function to excrete creatinine effectively and lead to creatinine retention in the body. Therefore, increase of serum creatinine indicates lowering GFR and is an important sign of kidney deterioration.

Figure 4:
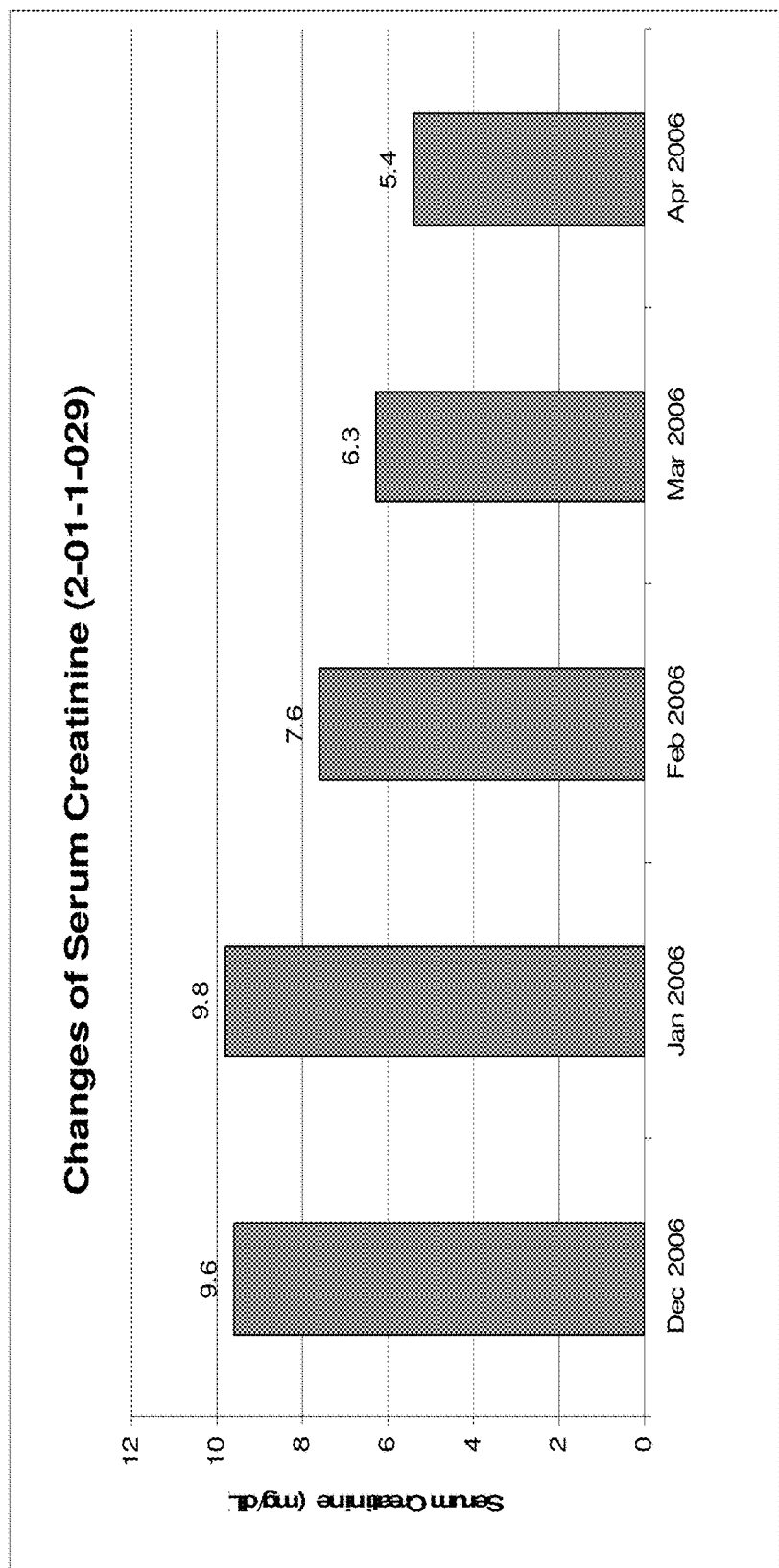
FIG. 4 shows the serum creatinine levels of a patient (patient code: 2-01-1-029) treated with 6 g/day of ferric citrate.
Figure 5:
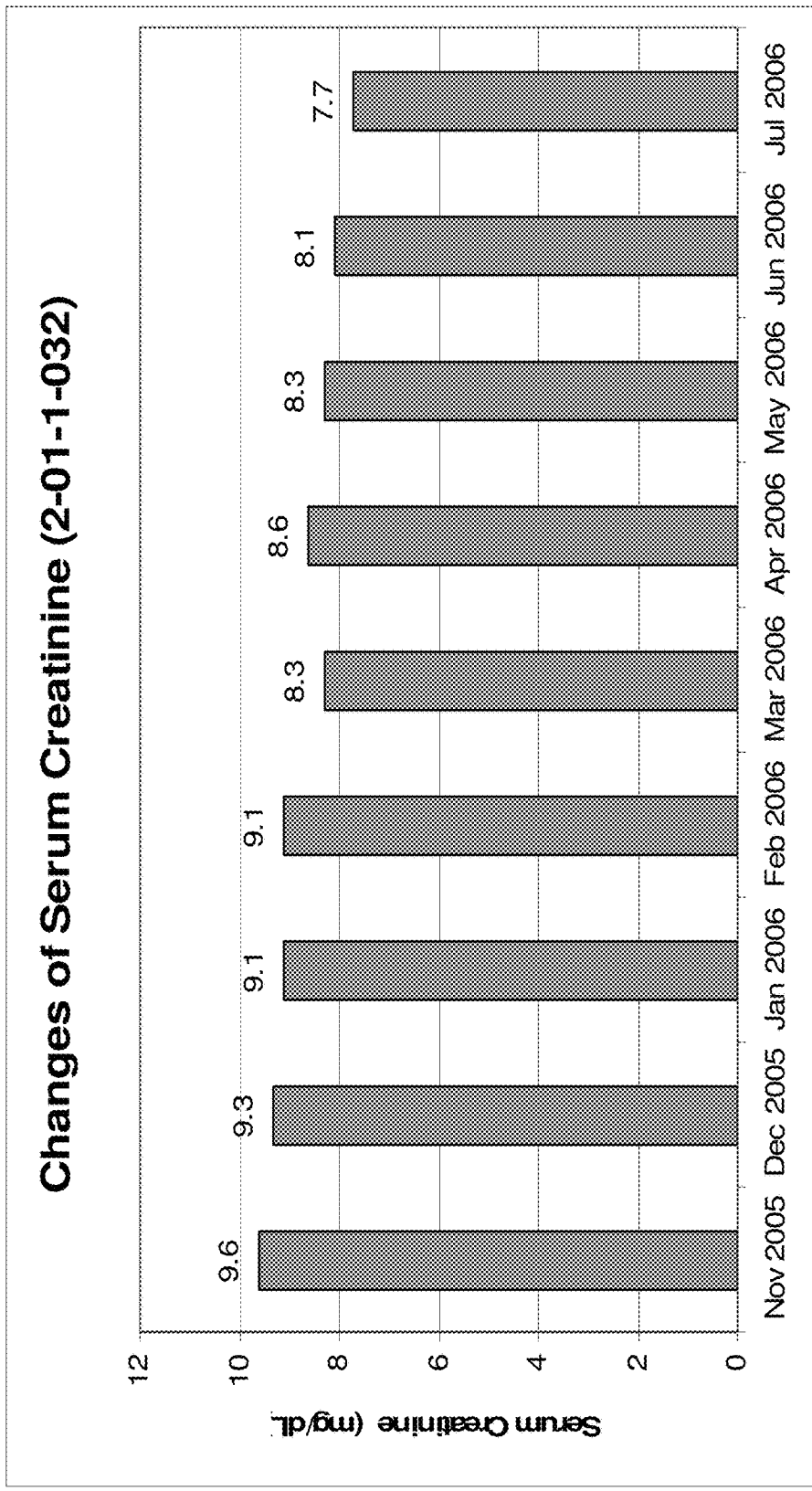
FIG. 5 shows the serum creatinine levels of a patient (patient code: 2-01-1-032) treated with 6 g/day of ferric citrate.

In an open-label extension of a Phase II clinical study: "randomized, double-blind, placebo-controlled, dose-ranging study of the effects of ferric citrate on serum phosphate in patients with end stage renal disease (ESRD)", some of the patients were administered 2-6 g/day of ferric citrate and serum creatinine level was monitored to assess kidney function. Several patients who received 6 g/day of ferric citrate appear to have a trend of decreased serum creatinine level, which implies ferric citrate may modify, delay, arrest or prevent the progression chronic kidney disease. Results from 2 patients are shown in FIGS. 4-5.

Example 3

Methods of Measuring Cornea Calcification

Figure 6:
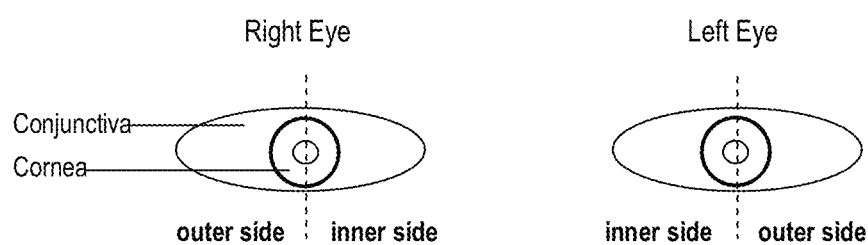
FIG. 6 shows the different regions of eye for eye examination.

Eye examinations were carried out by using a slit-lamp microscope which was connected to a digital camera (NIKON E995). Calcifications in the cornea occur close to the nasal and temporal sides of the corneal limbus and look like the band keratopathy of hypercalcemia. Observer photographed the inner side (close to nasal), outer side (close to temporal) or took a full view of the cornea where calcification was found (FIG. 6). Therefore, there were 1 to 2 pictures taken for each eye and resulted in collecting 2-4 pictures per patient per examination.

An image analysis software called "Image J" was used for data analysis. The image analysis software is developed to display, edit, analyze, process, save and print 8-bit, 16-bit and 32-bit images. It can calculate area and pixel value statistics of user-defined selections, measure distances and angles, and create density histograms and line profile plots. It supports standard image processing functions such as contrast manipulation, sharpening, smoothing, edge detection and median filtering. The software is developed at the Research Services Branch of the National Institute of Mental Health, an institute of the National Institutes of Health (NIH). The software can be downloaded from the NIH website.

Figure 7:
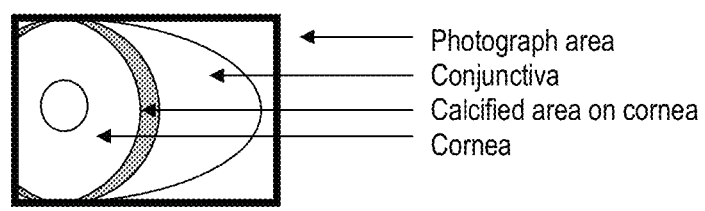
FIG. 7 shows an example photograph of cornea calcification.

The image analysis software is able to measure calcified area and total cornea area that are subjectively defined by the user. To estimate calcified area, the observer first loads the patient's eye picture on to the image software, crops the specific calcified region, and the software will measure the defined section accordingly (defined as how many pixels in that area). It should be noted that because the pictures were taken by focusing on one side of cornea, the photos usually did not capture complete image of a cornea. To estimate the size of the full cornea, the observer used the image software to crop a 90 degrees fan-shape area on the available cornea region on the picture subjectively, and then let the software calculate the size of this fan-shape area to represent ¼ of the full cornea. By multiply the number by four, the observer then got an estimate of total cornea area. An example photograph of cornea calcification is shown in FIG. 7.

Figure 8:
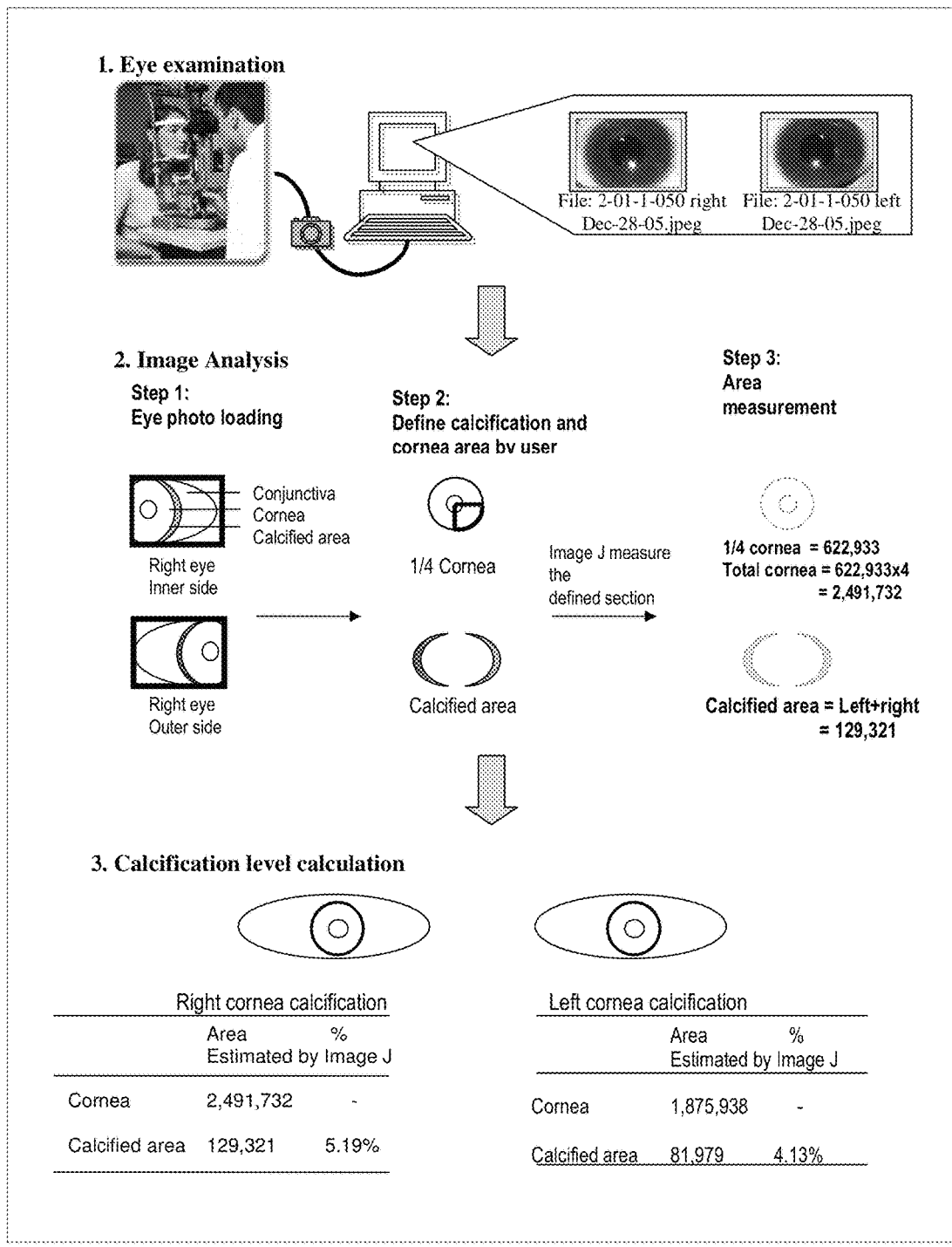
FIG. 8 shows an example of eye examination and calculation of cornea calcification.

The severity of cornea calcification was evaluated based on the percentage of the cornea surface occupied by calcification, i.e. % inner side calcification+% outer side calcification, wherein inner or outer side calcification is calculated as (calcified area on inner or outer cornea/total cornea area)×100. See FIG. 8.

Several factors may affect the calcification measurement of cornea:

(1) Different lag period of after treatment examination may result in variance between subjects as defined by the examiner.

(2) Photography factors such as the lightness of the environment, focal length, exposure time, brightness, light sensitivity (ISO value), resolution, picture contrast, etc were not controlled. These factors may influence the quality between pictures and hence affect the physician's judgment on accurately defining the calcified area between different photos.

(3) Image of cornea area was not standardized. Most photos only contained a partial view of cornea. To estimate the size of the total cornea area, the observer subjectively defined a 90 degree fan-shape area to extrapolate the size of a complete cornea by multiply the value by four.

(4) Different cameras were used in some pictures: the camera used in the baseline cornea measurement was accidentally out of order and another camera was on board to conduct some of the 2nd cornea measurements.

(5) The current method of using 2-dimensional area to estimate 3-dimensional calcification on the sphere structure of cornea is not absolutely accurate.

All of the above factors contribute to the error of the cornea calcification determination. However, the error has been minimized by the fact that all images were determined by a single evaluator, each patient served as its own control, and relative changes within each patient were examined.

Example 4

Ferric Citrate Reverses Cornea Calcification

Results from the Phase II study presented above indicate that ferric citrate can decrease serum Ca×P in a dose-dependent manner with minimum side effect. Because ocular calcification is among the most frequently observed soft-tissue calcification, treatment with ferric citrate was extended as open-label extension (OLE) after termination of the Phase II study to further investigated the effect of ferric citrate on ocular cornea calcification and its implication on soft-tissue calcification.

In this study, patients were referred to ophthalmic department for eye examination before and after ferric citrate treatment. All patients had their 1st eye examination few days before or on the first dosing day of the Phase II trial (baseline value for cornea calcification). The time for 2nd eye examination was varied. Some were examined right after the Phase II study and some were examined during the OLE period. Nonetheless, disregarding when the 2nd eye examination was taken, it must be obtained after a defined consecutive days of ferric citrate administration in order to be considered as valid value for determinating the effects of ferric citrate on the cornea calcification changes.

All patients from the ferric citrate Phase II clinical trial were followed with a drug free period for various length of time, and some patients then participated in the open-label extension treatment period. Each participating patients received two eye examinations performed by an ophthalmologist. Depending on the dates of the first and second eye examinations and the corresponding drug dosing period, not all participating patients can generate usable information. The accepted patients were those who had received consecutive dosing for at least 21 days. The period between the first and second eye examination was at least as long as the dosing period. The actual interval between the two eye examinations was not relevant for the purpose of this evaluation since the longer the time between the first and second eye examination, the higher the possibility of cornea calcification development, not the other way around. Therefore, the following results on estimating the effects of ferric citrate on the degree of cornea calcification change is indeed conservative if the interval between 1st and 2nd examination was longer than the drug treatment period.

A total of 12 patients produced data eligible for evaluation and the resulting data were listed in Table 6. Each patient had their left and right eyes examined and therefore 24 cornea calcification values were generated. Within these 12 patients, one received placebo and served as negative control. The other 11 patients received various period of consecutive active treatment (range 28 to 57 days) and generated 22 left and right eye cornea calcification values. Among the 11 patients who received active treatment, two (2) patients received ferric citrate dose level at 2 g/day, two (2) patients received ferric citrate dose level at 4 g/day while seven (7) patients received ferric citrate at 6 g/day dose level. Due to the limited number of patients involved in this evaluation, no formal statistics is needed and summary statistics are used herein.

The patient who received placebo was found to have cornea calcification worsened in an average of +6.55% (right eye worsened +1.28% and left eye worsened for +11.81%) during a period of 77 days between 1st and 2nd eye examination.

Within those 11 patients who received active treatment, their treatment period averaged 33 days and ranged from 28 to 57 days. The period between the 1st and 2nd examinations averaged 126 days and ranged from 50 to 217 days. Among these 11 patients, only 10 eye cornea calcification values exhibited worsened results (averaged +2.20%, range +0.08% to +6.98%). In contrast, one eye cornea calcification value remained unchanged while 11 eye cornea calcification values exhibited improvement (averaged −2.07%, ranged −0.08% to −10.21%). Examples of worsened or improved cornea calcification are shown in FIGS. 9-10.

The data presented above were extremely encouraging. Ferric citrate appears to delay or improve cornea calcification conditions. The results also imply ferric citrate treatment may improve various conditions of soft tissue calcification. Further clinical study may be performed to confirm the efficacy of ferric citrate on treatment of all soft tissue calcification conditions.

TABLE 6

Cornea Calcification In End Stage Renal Disease Patients Receiving Ferric Citrate Treatment

| Subject ID | Dose (g/day) | Interval between 1st and 2nd eye test (days) | Ferric citrate treatment period (days) | 1st eye test Calcified area on cornea (%) | 2nd eye test Calcified area on cornea (%) | Difference between $1^{st}$ and $2^{nd}$ tests (%) | Eye ID |
|---|---|---|---|---|---|---|---|
| 2-01-001 | Placebo | 77 | 77 | 4.19% | 5.47% | 1.28% | Right |
|  |  |  |  | 4.32% | 16.13% | 11.81% | Left |
| 2-01-1-002 | 2 g/day | 61 | 28 | 0.00% | 0.00% | 0.00% | Right |
|  |  |  |  | 3.90% | 3.75% | −0.15% | Left |
| 2-01-1-012 | 2 g/day | 66 | 28 | 14.90% | 4.69% | −10.21% | Right |
|  |  |  |  | 3.50% | 2.09% | −1.41% | Left |
| 2-01-1-048 | 4 g/day | 186 | 28 | 2.50% | 2.09% | −0.41% | Right |
|  |  |  |  | 1.85% | 2.01% | 0.16% | Left |
| 2-01-1-009 | 4 g/day | 50 | 28 | 0.51% | 1.00% | 0.49% | Right |
|  |  |  |  | 1.16% | 0.00% | −1.16% | Left |
| 2-01-1-050 | 6 g/day | 198 | 33 | 1.62% | 1.54% | −0.08% | Right |
|  |  |  |  | 0.86% | 1.62% | 0.76% | Left |
| 2-01-1-022 | 6 g/day | 217 | 57 | 7.21% | 7.29% | 0.08% | Right |
|  |  |  |  | 1.39% | 8.37% | 6.98% | Left |
| 2-01-1-068 | 6 g/day | 202 | 34 | 0.00% | 2.24% | 2.24% | Right |
|  |  |  |  | 1.05% | 3.09% | 2.04% | Left |
| 2-01-1-006 | 6 g/day | 50 | 28 | 32.43% | 29.27% | −3.16% | Right |
|  |  |  |  | 50.95% | 50.36% | −0.59% | Left |
| 2-01-1-004 | 6 g/day | 78 | 28 | 4.38% | 2.20% | −2.18% | Right |
|  |  |  |  | 2.50% | 1.10% | −1.40% | Left |
| 2-01-1-018 | 6 g/day | 75 | 28 | 40.85% | 38.86% | −1.99% | Right |
|  |  |  |  | 5.93% | 7.72% | 1.79% | Left |
| 2-01-1-042 | 6 g/day | 199 | 42 | 0.49% | 3.73% | 3.24% | Right |
|  |  |  |  | 0.67% | 4.91% | 4.24% | Left |

What is claimed is:

1. A method of reversing soft tissue calcification in a subject, comprising administering to said subject an effective amount of ferric citrate having a BET active surface area of at least about 16 m²/g, wherein soft tissue calcification is reversed.

2. The method of claim 1, wherein the ferric citrate has a BET active surface area of about 16 m²/g to about 20 m²/g.

3. The method of claim 1, wherein the soft tissue is selected from soft tissue in a joint, the skin, an eye, a heart valve, the myocardium, a coronary artery, a coronary arteriole, a kidney and a lung.

4. The method of claim 3, wherein the soft tissue is eye tissue.

5. The method of claim 1, wherein the ferric citrate is formulated for oral administration.

6. The method of claim 5, wherein the ferric citrate is formulated as a tablet, a powder, a suspension, an emulsion, a capsule, a lozenge, a granule, a troche, a pill, a liquid, a spirit or a syrup.

7. The method of claim 1, wherein the effective amount of ferric citrate is 2 grams per day.

8. The method of claim 1, wherein the effective amount of ferric citrate is 4 grams per day.

9. The method of claim 1, wherein the effective amount of ferric citrate is 6 grams per day.

10. The method of claim 1, wherein calcification is reversed by up to 40%.

11. The method of claim 1, wherein calcification is reversed by up to 56%.

12. The method of claim 1, wherein calcification is reversed by up to 67%.

13. The method of claim 1, wherein calcification is reversed by up to 100%.

* * * * *

UNITED STATES PATENT AND TRADEMARK OFFICE
CERTIFICATE OF CORRECTION

PATENT NO. : 9,889,113 B2  
APPLICATION NO. : 15/694876  
DATED : February 13, 2018  
INVENTOR(S) : Keith Chan, Winston Town and Shou Shan Chiang Page 1 of 1

It is certified that error appears in the above-identified patent and that said Letters Patent is hereby corrected as shown below:

On the Title Page

1. Add --(30) Foreign Application Priority Data  
Aug. 18, 2006 (WO) ............... PCT/US2006/032385--.

In the Specification

2. Column 4, Line 50, replace "PCT/US2006/032585" with --PCT/US2006/032385--.

3. Column 6, Line 16, replace "4 mg/cm/min" with --4 mg/cm2/min--.

4. Column 7, Line 60, replace "PCT/US2006/032585" with --PCT/US2006/032385--.

Signed and Sealed this  
Tenth Day of April, 2018

Andrei Iancu  
*Director of the United States Patent and Trademark Office*